United States Patent [19]

Foote et al.

[11] Patent Number: 5,057,078

[45] Date of Patent: * Oct. 15, 1991

[54] LOCKING SYRINGE

[75] Inventors: Jerrold L. Foote; Darla R. Gill; Fred P. Lampropolous, all of Salt Lake City; William Padilla, Bennion, all of Utah

[73] Assignee: Merit Medical Systems, Inc., Salt Lake City, Utah

[*] Notice: The portion of the term of this patent subsequent to Sep. 10, 2008 has been disclaimed.

[21] Appl. No.: 325,561

[22] Filed: Mar. 17, 1989

[51] Int. Cl.⁵ .......................................... A61M 29/00
[52] U.S. Cl. ...................................... 604/99; 604/98; 604/96; 604/224; 606/194
[58] Field of Search ............................... 128/675, 96; 604/97-100, 118, 103, 220, 109, 224, 225, 227, 207-208; 606/191, 192, 194

[56] References Cited

U.S. PATENT DOCUMENTS

| 383,940 | 6/1888 | Brinkerhoff. |
|---|---|---|
| 404,105 | 5/1889 | Overlach. |
| 466,125 | 2/1891 | Schirmer. |
| 577,682 | 2/1897 | Eissner. |
| 730,054 | 6/1903 | Sheets. |
| 1,661,818 | 3/1928 | Cook. |
| 1,707,880 | 4/1929 | Sheets. |

(List continued on next page.)

FOREIGN PATENT DOCUMENTS 545415 8/1957 Canada.
1242737 8/1960 France.

OTHER PUBLICATIONS

"ACS Accessories Offer Optimum Efficiency in Your Angioplasty Procedures," Eli Lilly and Company.
"Clearing the Path for a Healthy Heart," *Tristate: The Cincinnati Enquirer Magazine*, Oct. 23, 1988.
"Coronary Angioplasty," Krames Communications, 1985.
"Good News for People with Only Two Hands," SciMed Life Systems, Inc.
"Health-Critics of Angioplasty Worry About Inflated Success Claims," *U.S. News and World Report*, Jul. 25, 1988, p. 65.
"Inflation PRO: A New Dual-Support System for Angioplasty," Baxter Healthcare Corporation.
"PTCA Safe and Efficacious Performed Together With Diagnostic Angiography in Selected Cases," *Cardiovascular News*, May 1988, p. 8.
"USCI Wizard Disposable Inflation Device," C. R. Bard, Inc.

Primary Examiner—Stephen C. Pellegrino
Assistant Examiner—Michael Rafa
Attorney, Agent, or Firm—Workman, Nydegger & Jensen

[57] ABSTRACT

A syringe and method for use which may be selectively operated between a free position and a locked position. A triggering device configured with a trigger attached to the plunger of the syringe is employed. The triggering device includes a set of threads located on the plunger and a corresponding set of threads on the barrel of the syringe. Upon actuation of the trigger, the threads on the plunger are retracted from their position of engagement with the threads on the barrel, thereby placing the syringe in position for free movement of the plunger with respect to the barrel. The threads are biased in the engaged position. Thus, when the trigger is released, the threads on the plunger return to their position of engagement with the threads on the barrel. In the locked position, the plunger may be screwed into or out of the barrel by rotating the plunger, enabling the operator of the syringe to maintain strict control over the amount of pressure in the syringe. The triggering device employs a plurality of ramp and channel configurations which are disposed at approximately the same angle as the threads on the plunger and barrel. Thus, upon actuation of the triggering device, no net force results on the plunger which would cause movement of the plunger with respect to the barrel.

28 Claims, 2 Drawing Sheets

U.S. PATENT DOCUMENTS

| | | | |
|---|---|---|---|
| 2,656,836 | 10/1953 | Hickey | 128/218 |
| 2,672,866 | 3/1954 | Kater | 128/218 |
| 2,699,168 | 1/1955 | Lewis | 128/218 |
| 2,736,315 | 2/1956 | Feeney | 128/218 |
| 3,080,866 | 3/1963 | Friedman | 128/218 |
| 3,388,941 | 6/1968 | Marcus | 294/1 |
| 3,478,937 | 11/1969 | Solowey | 222/386 |
| 3,491,757 | 1/1970 | Arce | 128/221 |
| 4,057,050 | 11/1977 | Sarstedt | 127/2 |
| 4,063,662 | 12/1977 | Drummond | 222/31 |
| 4,254,773 | 3/1981 | Waldbillig | 128/348 |
| 4,267,846 | 5/1981 | Kontos | 128/765 |
| 4,439,185 | 3/1984 | Lundquist | 604/99 |
| 4,444,335 | 4/1984 | Wood | 222/43 |
| 4,466,426 | 8/1984 | Blackman | 128/1.1 |
| 4,568,335 | 2/1986 | Updike et al. | 604/224 |
| 4,583,974 | 4/1986 | Kokernak | 604/99 |
| 4,710,179 | 12/1987 | Haber et al. | 604/211 |
| 4,715,854 | 12/1987 | Vaillancourt | 604/191 |
| 4,723,938 | 2/1988 | Goodin et al. | 604/97 |
| 4,743,230 | 5/1988 | Nordquest | 604/97 |
| 4,758,223 | 7/1988 | Rydell | 604/98 |
| 4,825,876 | 5/1989 | Beard | 128/675 |
| 4,832,692 | 5/1989 | Box et al. | 604/99 |
| 4,838,864 | 6/1989 | Peterson | 604/118 |
| 4,919,121 | 4/1990 | Rydell et al. | 604/97 |
| 4,940,459 | 7/1990 | Noce | 604/98 |

LOCKING SYRINGE

BACKGROUND

1. Field of the Invention

The present invention relates to methods and apparatus for a syringe which operates selectively between a free mode and a threaded mode. More particularly, the present invention relates to a locking syringe and methods of use which incorporate a triggering device on the plunger of the syringe which may be actuated to retract threads located on the plunger of the syringe to enable the plunger to move with respect to the barrel in both a free mode and a locked, or threaded, mode.

2. The Background of the Invention

One of the most basic of the tools used by the medical practitioner is the syringe. Perhaps best known as an instrument used with a needle to inject medicine into a patient, the syringe has also been found useful in a variety of other applications. For example, syringes are particularly useful in performing angiographic procedures.

Angioplasty is a procedure for reducing the blockage which may occur in blood vessels. Over time, blood vessels may become partially or totally blocked due to buildup of cholesterol plaque along the walls of the vessel.

One location where plaque buildup is particularly dangerous is within the coronary arteries. The coronary arteries are those arteries which supply oxygen-rich blood to the heart. Buildup of plaque within the coronary arteries, a condition commonly referred to as coronary artery disease, can cause serious chest pain—angina—and, if not treated, may eventually cause heart failure.

Coronary angioplasty involves opening these blocked coronary arteries by inserting a balloon-tipped catheter into the artery. The balloon is inserted by making an incision usually in the groin or arm. A catheter is then inserted in a blood vessel exposed by the incision and threaded into the coronary artery.

An x-ray sensitive dye is injected into the coronary artery to enable the clinician to accurately position the catheter in the blocked portion of the artery. The catheter is inserted along the artery until the section of the catheter on which the balloon is located is positioned along the blocked portion of the artery.

A fluid is injected into the catheter to inflate the balloon. As the balloon is inflated, the plaque is compressed thereby expanding the narrowed artery. The clinician then withdraws the fluid from the balloon catheter, causing the balloon to deflate. The balloon catheter may then be removed from the patient.

It has been found that a syringe provides an effective tool for the introduction of fluid into the balloon catheter. However, because the pressure within the balloon must be carefully controlled during the angioplasty procedure, typical syringes having a plunger which may be freely depressed into the barrel are inadequate for this application.

If the pressure within the balloon is too great, the balloon may burst, a circumstance which usually requires immediate emergency surgery to correct. Some prior art attempts at designing a syringe which provides greater control over the pressures achieved in the balloon include providing a syringe which incorporates a plunger which is threadably connected to the barrel. Thus, the plunger may be slowly threaded into the barrel, resulting in a more controlled introduction of fluid into the balloon catheter.

A serious disadvantage to such syringes is the inability to freely and rapidly move the plunger in and out of the barrel. For example, a preferred method of deflating the balloon is to rapidly withdraw the plunger from the barrel to create a negative pressure, thereby causing the fluid to exit the balloon in an attempt to equilibrate the pressure within the balloon catheter. Withdrawing the plunger from the barrel of the syringe by "unscrewing" the plunger requires a great amount of time and, more significantly, results in reduced effectiveness in deflating the balloon.

In recognition of the desirability of a syringe having a plunger/barrel assembly capable of operating in both a "free" mode and a threaded mode, syringes have been developed i which address this problem. Most such syringes employ a thread engagement mechanism on the barrel of the syringe which can be actuated to selectively engage and disengage the threads on the plunger.

When the thread engagement mechanism is engaged, the syringe is "locked" into a threaded mode so that free movement of the plunger in and out of the barrel is not possible. In this locked position, the plunger may only be moved in and out of the barrel by rotating it—screwing it in or out of the barrel.

A serious design flaw which exists in some syringes employing a thread engagement mechanism on the barrel of the syringe is that the syringe is awkward to use. When using the syringe, one must grasp the barrel with one hand and depress the plunger with the other hand, taking care to steadily hold the syringe as the plunger is depressed. Depending on the location and direction of actuation of the thread engagement mechanism, it can be difficult to properly hold the syringe in a steady position and control the thread engagement mechanism at the same time.

An additional disadvantage to such syringes is that some prior art syringes require that the barrel of the syringe be aligned in a certain orientation before the thread engagement mechanism can be actuated. This makes the syringe more difficult to use because the user must first ensure that the engagement mechanism.

A potentially serious flaw exists in some syringe designs which incorporate a thread engagement mechanism which, when actuated, causes slight movement of the plunger. This movement of the plunger could cause an unwanted and potentially dangerous increase in the pressure within the balloon.

If the balloon were to be expanded beyond acceptable limits, the coronary artery being repaired might be expanded beyond its capacity to yield. Rupture of the coronary artery would require immediate emergency surgery to correct, and, depending on the severity of the rupture, might require immediate bypass surgery.

Many prior art syringes also suffer from the disadvantage that it is impossible to view the fluid within the syringe along its entire path into the balloon catheter. During angioplasty, it is important to prevent air bubbles from entering the balloon catheter. If an air bubble were to enter the balloon and the balloon were to burst, the resulting embolism could cause serious injury to the patient's heart and possibly result in the patient's death.

Apart from angioplasty, other medical applications also benefit from a "locking" syringe. For example, such a syringe could be advantageously employed in a biopsy procedure—removing a tissue or cell sample from a patient to be later tested and further examined in a laboratory.

Such a syringe could be utilized in this way to avoid having to subject the patient to more serious surgical procedures to obtain the sample. A needle could be attached to the syringe and inserted into the patient such that the end of the needle contacts the tissue desired to be sampled.

The plunger could then be rapidly withdrawn from the barrel of the syringe to create a negative pressure within the barrel of the syringe. The effect of the negative pressure would be to draw sample tissue into the needle. Utilizing a locking syringe enables the clinician to lock the plunger in this retracted position to preserve the negative pressure and free the clinician from having to hold the plunger in the desired position.

However, many of the problems and disadvantages discussed above with respect to angioplasty syringes also exist in syringes used for biopsy.

It will be appreciated, therefore, that what is needed in the art are methods and apparatus which may be used to inject a fluid under pressure and enable the operator of the syringe to maintain a significant degree of control over the pressures obtained.

It would be an advancement in the art to provide an apparatus and method for a syringe in which the plunger is
capable of selectively operating freely with respect to the barrel and operating in a "locked" or threaded mode.

It would also be an advancement in the art to provide an apparatus and method for such a syringe which is not awkward to operate because of positioning of a thread engagement mechanism located on the barrel of the syringe.

It would be a further advancement in the art if such an apparatus and method could be employed with a syringe such that the syringe may be actuated between a free mode and a threaded mode of operation irrespective of the orientation of the barrel of the syringe.

It would be yet a further advancement in the art to provide methods and apparatus for a syringe which would enable the syringe to be actuated between a free position and a threaded position without any movement of the plunger with respect to the barrel during such actuation.

It would be an additional advancement in the art if such a syringe and methods could be provided that would permit the user of the syringe to observe the existence of air bubbles within the syringe and along the path of the fluid being injected by the syringe.

The foregoing, and other features and objects of the present invention, are realized in the locking syringe disclosed and claimed herein.

BRIEF SUMMARY AND OBJECTS OF THE INVENTION

The present invention is directed to a locking syringe and its methods of use. The syringe includes a novel plunger and barrel combination which allows the syringe to be selectively operated between a free mode—wherein the plunger may be freely inserted into and withdrawn from the barrel—and a locked, or threaded, mode—wherein the plunger is locked by placing the plunger in threaded engagement with the barrel. In the locked position, the plunger may be screwed into or out of the barrel by rotating the plunger, thereby resulting in controlled movement of the plunger relative to the barrel. Thus, one operating the syringe in the locked mode can maintain precise control over the amount of pressure exerted by the syringe.

The syringe incorporates a triggering device which is actuated with a trigger located on the plunger. This convenient positioning of the trigger enables the clinician to easily actuate the triggering device using the same hand with which the plunger is actuated to operate the syringe, both in the free position and in the locked position.

In a preferred embodiment of the invention, the triggering device includes a set of threads and a series of channels A ramp corresponding to each channel is located along the handle of the syringe and is partially disposed within its corresponding channel. Upon actuation of the triggering device, the channels travel along the ramps, causing the threaded portion of the triggering device to be retracted from engagement with corresponding threads on the barrel. In this retracted position, the plunger is free to move with respect to the barrel.

Advantageously, the ramps and channels are disposed at an acute angle with respect to the vertical which is less than or equal to the angle of disposition with respect to the vertical of the primary teeth on the threads. Thus, as the triggering device is actuated and the channels slide along the ramps, the threads on the triggering device are retracted from the threads on the barrel without any net force resulting which would cause movement of the plunger with respect to the barrel.

When the syringe is designed for angioplasty, it may also be provided with an integral transducer means for measuring the amount of pressure exerted on fluid being injected by the syringe, as more particularly described in copending U.S. Pat. application Ser. No. 324,938, filed concurrently herewith, and which is incorporated herein by specific reference.

The barrel and tip of the syringe are made of a transparent material. Thus, the operator of the syringe may visually verify whether air bubbles are located within the liquid being injected with the syringe.

It is, therefore, a primary object of the present invention to provide a syringe which provides the operator of the syringe with the capability of maintaining precise control over the amount of pressure exerted by the syringe.

An additional object of the present invention is to provide a syringe and methods for use thereof by which selective operation in both a free mode and a locked, or threaded, mode, can be accomplished using the same hand used to actuate the plunger.

It is also an object of the present invention to provide such a syringe which incorporates a triggering mechanism having a trigger on the plunger of the syringe, thereby facilitating the use of the syringe.

It is a further object of the present invention to provide a syringe which may be actuated between the locked and free positions regardless of the orientation of the barrel of the syringe.

Still another object of the present invention is to provide such a locking syringe which incorporates a triggering device which may be actuated without resulting in any movement of the plunger with respect to the barrel.

Another important object of the present invention is to provide such a syringe which is made of a transparent material such that the entire path of the fluid being injected with the syringe may be viewed by the operator of the syringe to ensure that the liquid does not contain any air bubbles.

Other objects and advantages of the present invention will become more fully apparent upon reading the following detailed description and appended claims, and upon reference to the accompanying drawings, or by the practice of the invention.

DETAILED DESCRIPTION OF THE PREFERRED EMBODIMENTS

Figure 1:
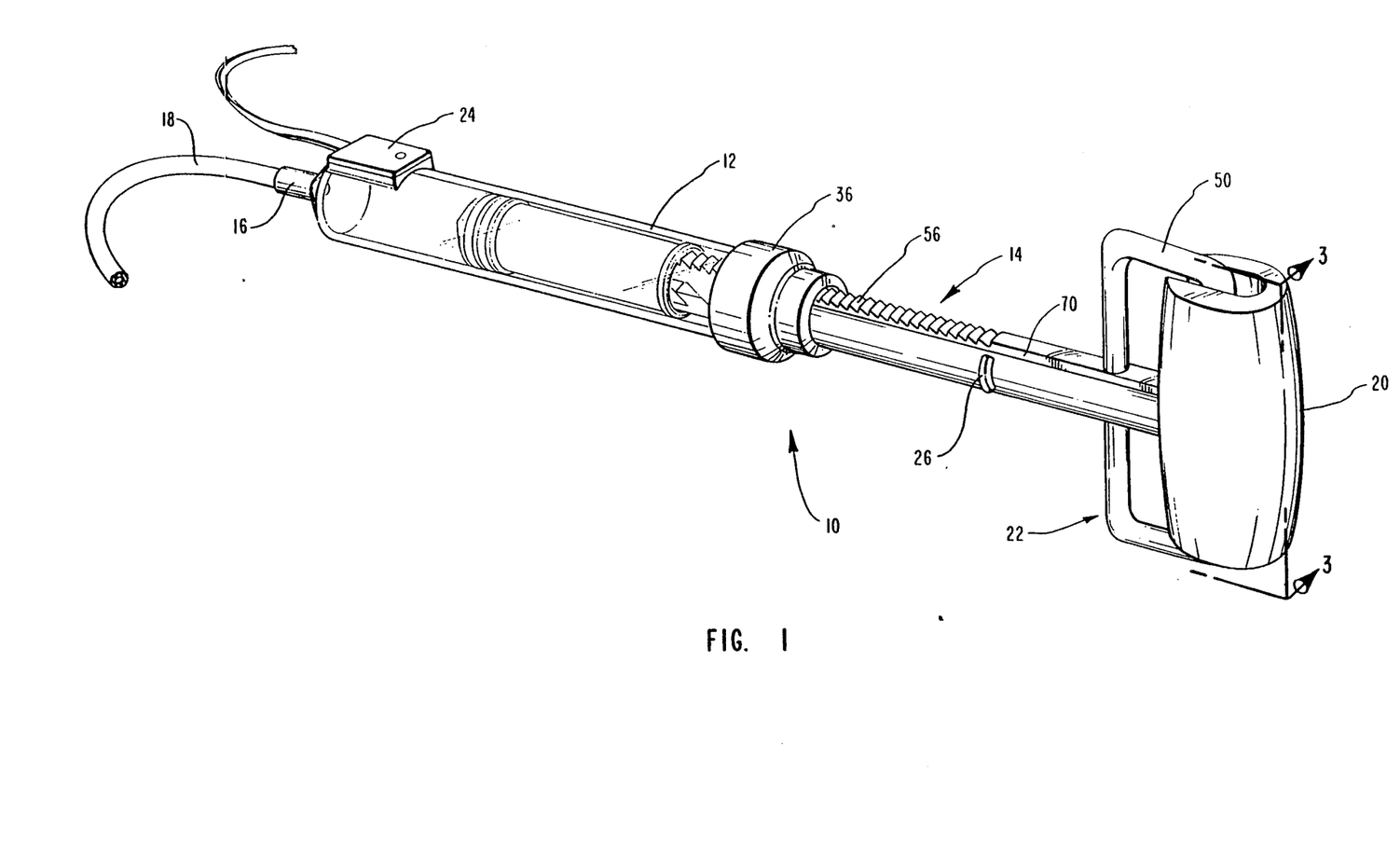
FIG. 1 is a perspective view of a presently preferred embodiment of the locking syringe of the present invention.

Reference is now made to the drawings wherein like parts are designated with like numerals throughout. Referring now to FIG. 1, one presently preferred embodiment of the present invention is illustrated and designated generally at 10.

The syringe 10 includes a barrel 12 and a plunger 14. The barrel 12 is equipped at one end with a tip 16. A piece of tubing 18 may be attached to the tip 16. The tubing 18 may be connected to a rotatable connector, such as a luer connector, and attached to a balloon catheter for use in angioplasty. Alternatively, a needle may be attached to the syringe at tip 16, thereby enabling the syringe to be used for a biopsy application. It will be appreciated that there are a variety of applications for the locking syringe of the present invention and, according to the application, an appropriate attachment may be attached to the syringe at tip 16.

With continued reference to FIG. 1, the plunger 14 further includes a handle 20 at one end of the plunger. The plunger 14 is also configured with a triggering device 22. As will be explained in greater detail below, the triggering device 22 may be actuated to selectively place the plunger in threaded engagement with the barrel or to enable the plunger to be freely moved in and out of the barrel.

The barrel 12 of the syringe further includes transducer means 24 in fluid communication with the interior of barrel 12 for measuring the fluid pressure within the barrel. In the presently preferred embodiment, the transducer means 24 is 3 located at the end of barrel 12, near tip 16, as illustrated in FIG. 1.

In order to effectively measure the pressure within the barrel 12, the transducer means 24 is ideally always in fluid contact, directly or indirectly, with the fluid in the interior of the barrel. To prevent the plunger from being inserted into the barrel and blocking the fluid contact between the transducer means and the barrel, a stop 26 is configured on the plunger 14.

The stop 26 thus acts to prevent the plunger 14 from being inserted into the barrel 12 beyond the location of the stop 26. It will be appreciated that a variety of other means may be employed for preventing the plunger from blocking fluid contact between transducer means 24 and the fluid in the interior of the barrel. For example, a ridge could be provided along the interior of the barrel adjacent the transducer means which would accomplish the same result.

Figures 2, 3, 3A, 4:
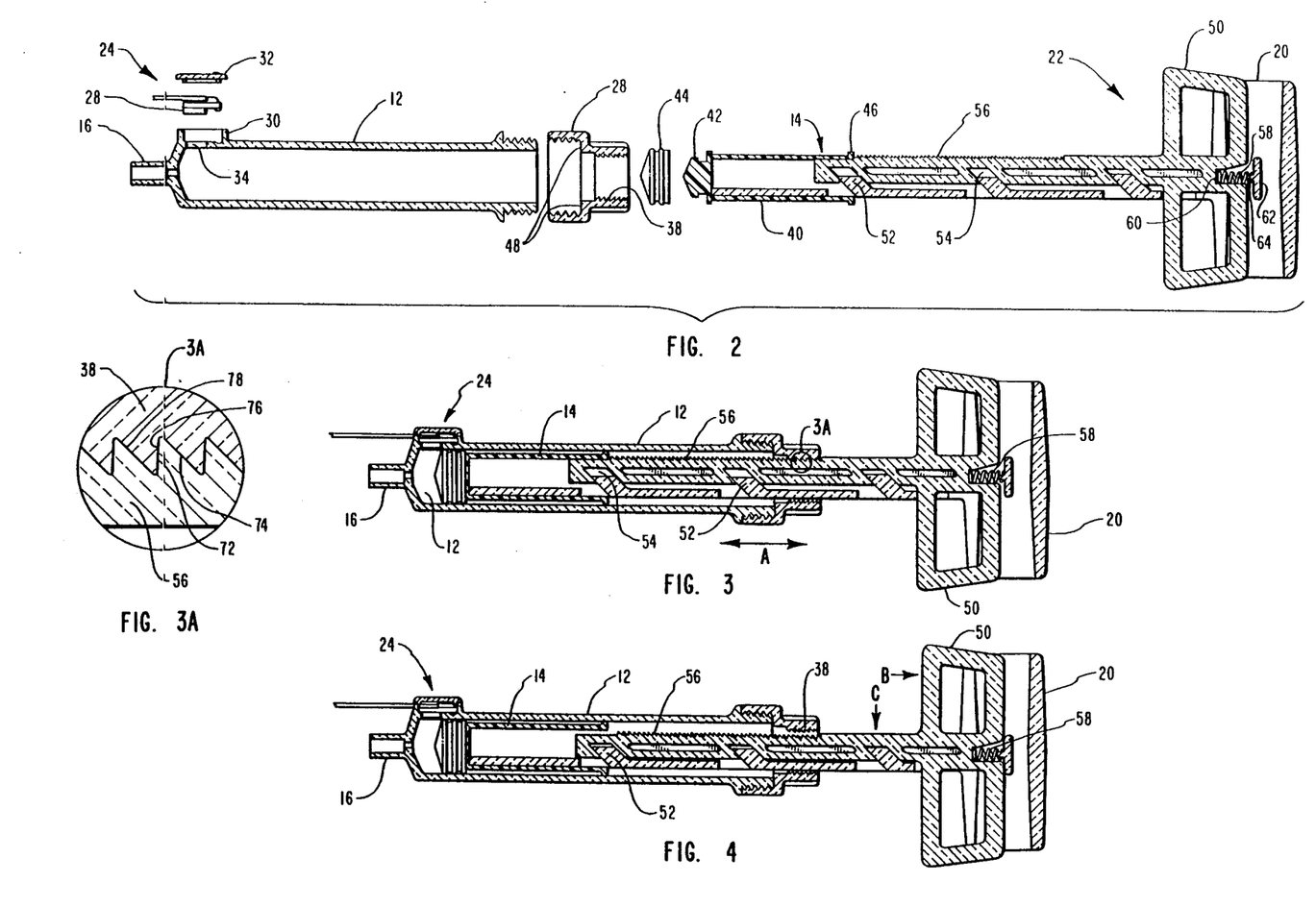
FIG. 2 is an exploded, cross-sectional view of the syringe illustrated in FIG. 1.
FIG. 3 is a cross-sectional view taken along lines 3—3 of FIG. 1, illustrating a syringe according to the present invention in the locked position.
FIG. 3a is an enlarged view of the internal and external threads illustrated in FIG. 3.
FIG. 4 is a cross-sectional view illustrating the syringe of FIG. 3 with the triggering device actuated and the syringe in the free position.

With reference now to FIG. 2, the transducer means 24 comprises, for example, a piezoresistive semiconductor integrated circuit chip 28 which mounts within a housing 30 integrally configured on the end of barrel 12. The transducer chip 25 and electrical cable 31 attached thereto are secured in housing 30 with a suitable potting compound, and a transducer cover 32 is provided to enclose the entire assembly in housing 30. A small opening 34 permits the fluid contact between the transducer chip 25 and the fluid in the interior of the barrel 12. As discussed above, stop 26 serves as a means to prevent the plunger from being inserted into the barrel to the point where bulb 44 would cover opening 34.

With continued reference to FIG. 2, the barrel 12 further includes a cap 28 which is threadably connected to one end of the barrel. Cap 28 is provided to facilitate assembly of the syringe. Cap 28 also includes a set of internal threads 38 which, as will be explained in greater detail below, may engage a corresponding set of threads on the plunger.

The plunger 14 is configured with a collar 40 having a bulb adaptor 42 at one end. The function and configuration of collar 40 is set forth in greater detail in copending U.S. Pat. application Ser. No. 07/173,447, filed Mar. 25, 1988, entitled DISPOSABLE CONTROL SYRINGE. A rubber bulb 44, such as those known in the art, is attached to the bulb adaptor 42.

In operation, the collar 40 of the plunger is always located within the barrel 12. Means are provided on the plunger to retain the collar 40 within the barrel. It is presently preferred that a disc 46 be configured on the end of collar 40 for this purpose. As the plunger is retracted out of the barrel 12, the disc 46 will engage lip 48 of the cap 28 to prevent further retraction of the plunger.

Still referring to FIG. 2, the triggering device 22 includes a trigger 50 in connection with the plunger 14. In a presently preferred embodiment, the trigger 50 is attached to the handle 20 to facilitate actuating the trigger with the same hand used to grasp the handle. It will be appreciated that the trigger 50 may also be disposed at various locations along the plunger 14.

The triggering device further includes a series of ramps 52 and a corresponding channel 54 for each ramp. Although in a presently preferred embodiment of the invention three sets of ramps and channels are employed, it will be appreciated that the number of ramps and channels is largely a matter of design choice. It has been found that increasing the number of ramps and channels may lend stability to the plunger and prevent unwanted deflection in the triggering device. The ramps 52 are disposed at least partially within their corresponding channels 54 at all times during the operation of the syringe.

In a preferred embodiment of the triggering device, a set of external threads 56 is configured on one side of the triggering device. The external threads 56 are configured such that they may threadably engage internal threads 38 located within cap 28. FIG. 1 illustrates that the external threads 56 are noncontinuous; that is, the tooth pattern does not continue around the threads to connect adjacent teeth to one another.

The triggering device is further configured with means for biasing the external threads 56 into threaded engagement with internal threads 38 and means for biasing the triggering device in a nonactuated position. One presently preferred mechanism for accomplishing this function is to employ a spring 58, as illustrated in FIG. 2, which rests between a groove 60 in trigger 50 and against a post 62 attached to handle 20.

The post 62 includes a nib 64 which fits inside the end of the spring resting against post 62. The nib 64 assists in positioning spring 58 against post 62 and preventing the spring from sliding along the post. Thus, post 62 and nib 64 act to properly position the trigger with respect to the handle and assist in preventing any lateral movement of the trigger with respect to the handle.

The operation of the locking syringe may be best explained with reference to FIGS. 3, 3A, 4. In FIG. 3, a locking syringe according to the present invention is illustrated in the locked, or threaded, position. In the "locked" position, the plunger 14 is in threaded engagement with the barrel 12 by the engagement of external threads 56 and internal threads 38. Thus, a force applied to the handle 20 of the syringe along the longitudinal direction (in the direction of arrow A) will not result in any movement of the plunger with respect to the barrel.

In the locked position, the plunger may, however, be moved in and out of the barrel 12 by rotating the handle 20. Depending on the pitch of the threads 56 and 38, the plunger will move a predetermined longitudinal distance with each rotation of the handle 20. In some applications, such as angioplasty, when the syringe is used to exert a controlled pressure, the ability to obtain slight longitudinal movements of the plunger are necessary for obtaining and exactly controlling the desired pressures.

FIG. 4 illustrates the syringe of the present invention with the triggering device actuated to place the syringe in the "free" mode of operation. With the triggering device so actuated, a longitudinally directed force applied to the handle 20 of the syringe will result in movement of the plunger 14 either in or out of the barrel 12. Thus, rapid movement of the plunger with respect to the barrel may be obtained with the syringe in the free position.

Many applications requiring a locking syringe also require that the syringe be capable of operating in such a free position. For example, when performing angioplasty, it is first necessary to fill the balloon catheter with a liquid before applying pressure on the liquid to expand the balloon within the blocked blood vessel. Initially filling the balloon catheter can be quickly and easily accomplished with the syringe in the free position.

Also, when the angioplasty procedure is completed and it is desired to deflate the balloon, the balloon may be most efficiently deflated by creating a negative pressure within the syringe which will act to extract the liquid out of the balloon catheter, thereby deflating the balloon. The creation of negative pressure within the syringe can be effectively accomplished with the catheter in the free position.

Still referring to FIG. 4, the triggering device is actuated by applying a force on the trigger 50 in the direction of arrow B. Unlike prior art type syringes, this may be advantageously done by the clinician with a one-handed movement and using the same hand that moves the syringe plunger. The clinician grasps handle 20 and by squeezing the handle 20 is able to apply a force on the trigger in the direction of arrow B and an equal and opposite force on the handle 20. Thus, there is no resulting net force on the plunger which would tend to move the plunger in or out of the barrel. The force applied to the trigger acts to compress spring 58 and causes the channels 54 to slide down the ramps 52.

Figure 5:
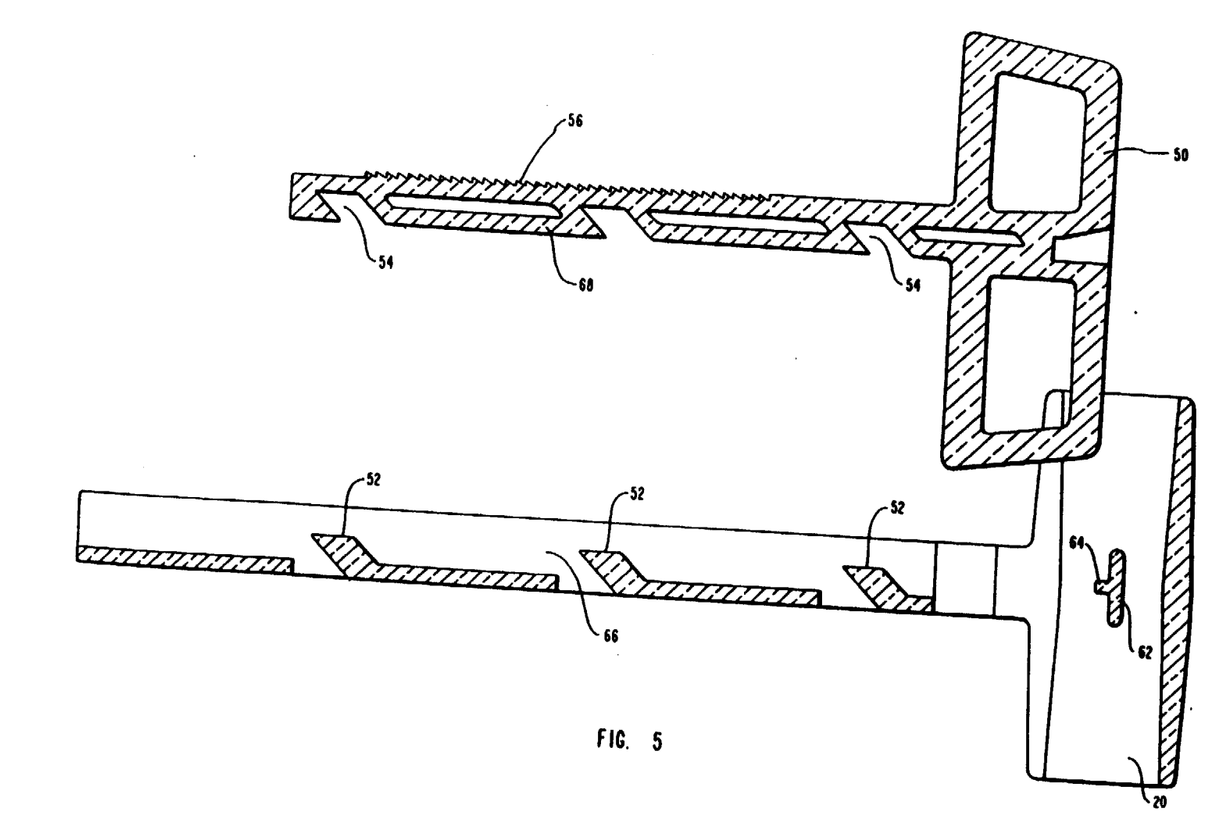
FIG. 5 is a cross-sectional view illustrating the separate pieces which comprise a presently preferred embodiment of the handle and triggering device according to the present invention.

The two primary components which comprise the triggering device are separately illustrated in FIG. 5. As illustrated in FIG. 5, a circular section 66 is attached to the handle 20. A threaded insert 68 attached to trigger 50 lies within an extended channel 70 (see FIG. 1) configured along the longitudinal length of the circular section 66. When assembled, as illustrated in FIG. 4, the channels 54 each engage a ramp 52.

As the triggering device is actuated by applying a force to trigger 50 in the direction of arrow B, the threaded insert 68 is forced to travel along the ramps 52. As the channels travel along the ramps, the external threads 56 located on the threaded insert are retracted from engagement with the internal threads 38.

The direction of retraction of the external threads 56 is dictated by the angle of the ramps. For example, a presently preferred angle of disposition of the ramps is approximately 45 degrees with respect to the vertical, as viewed in FIG. 4. Thus, as the external threads 56 are retracted upon actuation of the triggering device, the threads move both longitudinally in the direction of arrow B and laterally in the direction of arrow C.

In some applications for which a locking syringe, such as a syringe according to the present invention, is utilized, it is necessary that the triggering device may be actuated without any resulting movement of the plunger with respect to the barrel. To prevent any movement of the plunger with respect to the barrel as the external threads are retracted from engagement with the internal threads, the external and internal threads are positioned at an angle greater than or equal to the angle of disposition of the ramps 52 and channels 54.

FIG. 3A is an enlarged view of the internal and external threads of FIG. 3 and illustrates the nonsymmetry of the teeth. As can be observed in FIG. 3A, each tooth of the external threads 56 has a leading edge 72 and a trailing edge 74. Also, the teeth on internal threads 38 have a leading edge 76 and a trailing edge 78. Leading edges 72 and 74 of external threads 56 and internal threads 38, respectively, are preferably disposed at an equal but opposite angle with respect to each other, such that the teeth properly mesh. The same is true of trailing edge 74 of external threads 56 and trailing edge 78 of internal threads 38.

In a preferred embodiment, trailing edges 74 and 78 are disposed at the same acute angle with respect to the vertical as the acute angle of disposition with respect to the vertical of ramps 52 and channels 54. Thus, as the threads are moved from a position of disengagement to a position of engagement, there is no possibility that any teeth on exterior threads 56 will contact the trailing edge 78 of the teeth on the internal threads 38 and thereby cause movement of the plunger into the barrel. Such movement would result in an increase in the pressure being exerted by the syringe which, as noted above, is not acceptable for certain applications of a locking syringe.

If slight increases of pressure within the barrel of the syringe as the triggering device is actuated can be tolerated for certain applications, a variety of combinations of angles may be utilized. It has been found that a 45 degree ramp angle is preferable because it most efficiently utilizes the force applied to the handle to actuate the triggering device.

The leading edges 72 and 76 of the threads preferably are disposed at an angle of approximately two degrees with respect to the vertical (the direction of arrow C). This two degree draft is primarily to assist in removing the parts from their molds during the manufacturing process when the parts are molded from plastic.

In order to prevent the plunger 14 from ratcheting back when a substantial pressure is built up inside the barrel of the syringe (pressures of up to approximately 20 atmospheres are not uncommon for angioplasty applications), the ramps are canted to the left, as viewed in FIG. 3, or towards the tip of the barrel. However, for other applications, it may be desirable to reverse the orientation of the ramps. For example, when the locking syringe is used primarily or exclusively for creating negative pressure, the ramps should be canted to the right, as viewed in FIG. 3, or away from the tip, to prevent the plunger from ratcheting into the barrel as substantial negative pressures are developed.

When it is desired to release the syringe from the free position and have it return to the locked position, the force being applied to trigger 50 is released. Acting under the biasing force of spring 58, the threaded insert 68 will travel up the ramps 52 and return the external threads 56 to their position of threaded engagement with the internal threads 38, as illustrated in FIG. 3.

With the trigger 50 attached to the plunger 14 of the syringe, the triggering device may be actuated regardless of the orientation of the barrel. To actuate the triggering device, the operator of the syringe need only grasp the barrel with one hand and hold the handle with the other hand. The trigger may then be easily actuated with the hand which is holding the handle.

It will be appreciated by one skilled in the relevant art that a syringe according to the present invention may be made of a variety of materials. However, it is presently preferred that the barrel 12, including the tip 16, be made of a transparent material, such as plastic. Thus, the operator of the syringe can visually ascertain whether any air bubbles exist in the barrel.

It will be appreciated that the apparatus and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A locking syringe, comprising:
   a barrel including a set of internal threads;
   a plunger disposed at lest partially within the barrel, the plunger comprising a set of external threads disposed on at least a portion of said plunger along the longitudinal axis thereof and which may threadably engage the set of internal threads; and
   a triggering means attached to the plunger for selectively retracting said external threads, such that when the triggering means is actuated, the external and internal threads maintain a position of disengagement, thereby enabling the plunger to be freely moved with respect to the barrel.

2. A locking syringe as defined in claim 1, wherein the triggering means may be actuated by applying equal and opposite forces to the triggering means and plunger.

3. A locking syringe as defined in claim 2, wherein the plunger further comprises a handle and the triggering means is attached to the handle.

4. A locking syringe as defined in claim 1, wherein the triggering means comprises means for preventing movement of the plunger with respect to the barrel when the triggering means is actuated.

5. A locking syringe as defined in claim 1, wherein the triggering means comprises means for retracting the external threads from engagement with the internal threads in a direction towards the handle and at an angle with respect to the longitudinal axis of the barrel.

6. A locking syringe as defined in claim 5, wherein the external threads are noncontinuous.

7. A locking syringe as defined in claim 1, wherein the triggering means is situated relative to said plunger such that it may be actuated without regard to its orientation with respect to the barrel.

8. A locking syringe, comprising:
   a barrel including at set of internal threads;
   a plunger disposed at least partially within the barrel, the plunger comprising a set of external threads disposed on at least a portion of said plunger along the longitudinal axis thereof and which may threadably engage the set of internal threads; and
   a triggering means for selectively retracting said external threads such that when the triggering means is actuated, the external threads are retracted from their position of engagement with the internal threads to a position of disengagement, thereby enabling the plunger to be freely moved with respect to the barrel.

9. A locking syringe as defined in claim 8, further comprising means for biasing the st of external threads into threaded engagement with the set of internal threads.

10. A locking syringe as defined in claim 8, wherein the triggering means is situated relative to said plunger such that it may be actuated without regard to the orientation of the barrel.

11. A locking syringe as defined in claim 8, wherein the internal and external threads each comprise a leading edge and a trailing edge disposed at different angles with respect to a line perpendicular to the longitudinal axis of the plunger.

12. A locking syringe as defined in claim 11, wherein the triggering means comprises means for retracting the external threads at an angle with respect to the length of the barrel upon actuation of the triggering means such that there is no movement of the plunger with respect to the barrel as the triggering means is actuated.

13. A locking syringe as defined in claim 12, wherein the retracting means comprises at least one ramp and a corresponding channel which engages the ramp.

14. A locking syringe as defined in claim 13, wherein the channel is disposed at an acute angle with respect to a line perpendicular to the longitudinal axis of the plunger which is less than or equal to the acute angle of disposition with respect to a line perpendicular to the longitudinal axis of the plunger of the trailing edge of the external threads.

15. A locking syringe as defined in claim 14, wherein the channel and the trailing edge of the external threads ar disposed at the same acute angle with respect to a line perpendicular to the longitudinal axis of the plunger.

16. A syringe which may be selectively operated between a free position and a locked position, comprising:
   a barrel including a set of internal threads;
   a tip disposed at a first end of the barrel;
   a plunger disposed at least partially within the barrel, the plunger including a set of noncontinuous external threads which may threadably engage the set of internal threads;
   a handle attached to the plunger; and
   a triggering means attached to the handle for retracting the external threads from their position of engagement with the internal threads to a position of disengagement, thereby enabling the plunger to be freely moved with respect to the barrel.

17. A syringe which may be selectively operated between a free position and a locked position as defined in claim 16, wherein the triggering means comprises means for preventing movement of the plunger with respect to the barrel upon actuation of the triggering means.

18. A syringe which may be selectively operated between a free position and a locked position as defined in claim 16, wherein the triggering means comprises means for retracting the external threads from engagement with the internal threads in a direction towards the handle and at an angle with respect to the longitudinal axis of the barrel.

19. A syringe which may be selectively operated between a free position and a locked position as defined in claim 16, wherein the internal and external threads comprise a leading edge and a trailing edge disposed at different angle with respect to a line perpendicular to the longitudinal axis of the plunger.

20. A syringe which may be selectively operated between a free position and a locked position as defined in clam 18, wherein the triggering means comprises at least one ramp and a corresponding channel which engages the ramp.

21. A syringe which may be selectively operated between a free position and a locked position as defined in claim 20, wherein the channel and the trailing edge of the external threads are disposed at the same angle with respect to a line perpendicular to the longitudinal axis of the plunger.

22. A syringe which may be selectively operated between a free position and a locked position as defined in claim 21, further comprising means for biasing the triggering means in a nonactuated position.

23. A syringe which may be selectively operated between a free position and a locked position as defined in claim 16, wherein the barrel comprises an interior chamber and wherein the syringe further comprises means in open connection with the interior chamber of the barrel for measuring pressure in the interior chamber of the barrel.

24. A syringe which may be selectively operated between a free position and a locked position as defined in claim 23, wherein said measuring means comprises a pressure sensor attached to the first end of the barrel.

25. A syringe which may be selectively operated between a free position and a locked position as defined in claim 24, further comprising means for preventing the plunger from blocking the open connection between the pressure sensor and the interior chamber of the barrel.

26. A syringe which may be selectively operated between a free position and a locked position as defined in claim 25, wherein the means for preventing the plunger from blocking the open connection between the pressure sensor and the interior chamber of the barrel comprises a stop attached to the plunger.

27. A syringe which may be selectively operated between a free position and a locked position as defined in claim 16, wherein the plunger comprises means for retaining the plunger at least partially disposed within the barrel.

28. A syringe which may be selectively operated between a free position and a locked position as defined in claim 16, wherein the tip and barrel are transparent such that the existence of air bubbles within the tip and barrel may be observed by one using the syringe.

* * * * *

UNITED STATES PATENT AND TRADEMARK OFFICE
CERTIFICATE OF CORRECTION

PATENT NO. : 5,057,078

DATED : October 15, 1991

INVENTOR(S) : JERROLD L. FOOTE et al.

It is certified that error appears in the above-identified patent and that said Letters Patent is hereby corrected as shown below:

Column 2, line 17, "i" should be deleted
Column 2, line 43, after "that the" insert --syringe is properly aligned before actuating the thread--
Column 3, line 27, after "is" sentence should continue on the same line
Column 4, line 13, after "channels" insert --.--

Column 8, line 14, after "20" insert --.--
Column 10, line 46, "st" should be --set--
Column 11, line 8, "ar" should be --are--
Column 11, line 46, "clam 18" should be --claim 18--

Signed and Sealed this

Sixteenth Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,057,078

DATED : October 15, 1991

INVENTOR(S) : JERROLD L. FOOTE, et al.

It is certified that error appears in the above-identified patent and that said Letters Patent is hereby corrected as shown below:

Figure 5 of the drawing, should be deleted to appear as per attached sheet.

Signed and Sealed this

Twenty-fifth Day of March, 1997

BRUCE LEHMAN

*Attest:*

*Attesting Officer*        *Commissioner of Patents and Trademarks*

FIG. 5